United States Patent
Easson et al.

(10) Patent No.: US 11,707,199 B2
(45) Date of Patent: Jul. 25, 2023

(54) MEASUREMENT SYSTEM WITH CONTROLLED PRESSURE RAMP

(71) Applicant: Maxim Integrated Products, Inc., San Jose, CA (US)

(72) Inventors: Craig Alexander Easson, San Jose, CA (US); John Philip Hanks, Austin, TX (US)

(73) Assignee: MAXIM INTEGRATED PRODUCTS, INC., San Jose, CA (US)

( * ) Notice: Subject to any disclaimer, the term of this patent is extended or adjusted under 35 U.S.C. 154(b) by 185 days.

(21) Appl. No.: 17/009,220

(22) Filed: Sep. 1, 2020

(65) Prior Publication Data

US 2021/0068682 A1 Mar. 11, 2021

Related U.S. Application Data (60) Provisional application No. 62/897,639, filed on Sep. 9, 2019.

(51) Int. Cl.
*A61B 5/021* (2006.01)
*A61B 5/00* (2006.01)
*A61B 5/0225* (2006.01)

(52) U.S. Cl.
CPC ...... *A61B 5/02141* (2013.01); *A61B 5/02255* (2013.01); *A61B 5/681* (2013.01); *A61B 5/6843* (2013.01); *A61B 5/6831* (2013.01)

(58) Field of Classification Search
CPC . A61B 5/02141; A61B 5/02255; A61B 5/681; A61B 5/6843; A61B 5/6831
See application file for complete search history.

(56) References Cited

U.S. PATENT DOCUMENTS

| | | | |
|---|---|---|---|
| 2002/0095092 A1* | 7/2002 | Kondo | A61B 5/02241 600/490 |
| 2011/0021932 A1* | 1/2011 | Kim | A61B 5/02233 600/499 |

(Continued)

FOREIGN PATENT DOCUMENTS

KR   10-2018-0047563 A   5/2018

OTHER PUBLICATIONS

David Monras, a novel smart jacket for blood pressure measurement based on shape memory alloys, ResearchGate, Jul. 3, 2019, Universitat Politècnica de Catalunya, https://www.researchgate.net/publication/334193951.

*Primary Examiner* — Eric F Winakur
*Assistant Examiner* — Abid A Mustansir
(74) *Attorney, Agent, or Firm* — Robert Crownover (57) ABSTRACT

A measurement system and method of manufacture can include: a pressure resistant structure; a pressure inducer coupled to the pressure resistant structure, the pressure inducer having an engaged configuration, the engaged configuration of the pressure inducer increasing pressure exerted on a portion of a user in contact with the pressure resistant structure; a light source coupled to the pressure resistant structure; an optical sensor coupled to the pressure resistant structure and configured to detect a signal from the light source; a pressure sensor coupled to the pressure resistant structure, the pressure sensor configured to detect the pressure exerted on the portion of the user in contact with the pressure inducer; and a processor coupled to the optical sensor and the pressure sensor, the processor configured to correlate volumetric data from the optical sensor with pressure data from the pressure sensor and to provide a blood pressure measurement.

18 Claims, 4 Drawing Sheets

(56) References Cited

U.S. PATENT DOCUMENTS

2017/0119314 A1    5/2017   Just et al.
2017/0157431 A1    6/2017   Cheatham, III et al.
2018/0338721 A1   11/2018   Wang et al.

* cited by examiner

FIG. 8

MEASUREMENT SYSTEM WITH CONTROLLED PRESSURE RAMP

CROSS-REFERENCE TO RELATED APPLICATION(S)

This claims priority benefit to all common subject matter of U.S. Provisional Patent Application No. 62/897,639 filed Sep. 9, 2019. The content of this application is incorporated herein by reference in its entirety.

TECHNICAL FIELD

This disclosure relates to electronic physiological measurement systems, more particularly to measurement systems utilizing pressure inducers for controlled pressure ramps in blood pressure measurements.

BACKGROUND

The rapidly growing market for portable and wearable electronic devices represents one of the largest potential market opportunities for next generation biological sensors. These devices have unique attributes that have significant impacts on their design and manufacture, in that they must be generally small, lightweight, and rich in functionality, and they must be produced in high volumes at relatively low cost.

One extension of the portable and wearable electronics industry is the biological sensor industry, which includes optical sensors for measuring heart rate, blood pressure, and peripheral oxygen, for example. The biological sensor industry, similar to the portable and wearable electronics industry, has witnessed ever-increasing commercial competitive pressures, along with growing consumer expectations and the diminishing opportunities for meaningful product differentiation in the marketplace.

Sensor system size, sensor system design, and sensor system materials are evolving technologies at the very core of next generation biological sensors. These next generation biological sensors are outlined in road maps for development of next generation products. Competitive next generation sensor systems should increase signal to noise ratio, decrease costs, and operate with increased sensor performance. Importantly, for some industry segments including wearable rings and watches, achieving new measurements with smaller form factors and reduced power requirements is critical.

There have been many approaches to addressing the advanced requirements of biological sensor systems and optical sensor systems with successive consumer product releases. Many industry road maps have identified significant gaps between the current sensor capability and design requirements for future products.

With the advance of biological sensor systems in the wearable electronic market, many measurements have been incorporated into applications utilizing sensors onboard an electronic device. While measurement systems, incorporated into electronic devices, can provide many advantages in terms of cost, time, convenience, and expanded measurement sets, many limitations still arise.

Illustratively, for example, blood pressure measurements at one time were limited to trained professionals utilizing arm pressure cuffs. Blood pressure measurements have been incorporated into applications utilizing sensors onboard an electronic device. One previous approach to blood pressure monitoring is the oscillometric finger pressing method. This method utilizes an on-board photo detector and a strain gauge array to estimate blood pressure.

The primary limitation with the finger pressing method is controlled pressure input. Controlled pressure input can be critical to an accurate blood pressure measurement. In the finger pressing method, the pressure input is left entirely to a user, which can lead to many inconsistencies and indecipherable data.

As consumer electronic devices evolve to utilize and incorporate more physiological data into medical applications and athletic applications, the pressure to push the technological envelope becomes increasingly challenging. More significantly, with the ever-increasing complexity, the potential risk of error increases greatly during manufacture.

In view of the ever-increasing commercial competitive pressures, along with growing consumer expectations and the diminishing opportunities for meaningful product differentiation in the marketplace, it is critical that answers be found for these problems. Additionally, the need to reduce costs, reduce production time, improve efficiencies and performance, and meet competitive pressures, adds an even greater urgency to the critical necessity for finding answers to these problems.

Thus, a need remains for measurement systems incorporating consistent pressure inputs, at low cost, and with low power requirements. Solutions to these problems have been long sought, but prior developments have not taught or suggested any complete solutions and, thus, solutions to these problems have long eluded those skilled in the art.

BRIEF DESCRIPTION OF THE DRAWINGS

The measurement system with controlled pressure ramp is illustrated in the figures of the accompanying drawings which are meant to be exemplary and not limiting, in which like reference numerals are intended to refer to like components, and in which.

DETAILED DESCRIPTION

In the following description, reference is made to the accompanying drawings that form a part hereof, and in which are shown by way of illustration, embodiments in which the measurement system may be practiced. It is to be understood that other embodiments may be utilized and structural changes may be made without departing from the scope of the measurement system.

When features, aspects, or embodiments of the measurement system are described in terms of steps of a process, an operation, a control flow, or a flow chart, it is to be understood that the steps can be combined, performed in a different order, deleted, or include additional steps without departing from the measurement system as described herein.

The measurement system is described in sufficient detail to enable those skilled in the art to make and use the measurement system and provide numerous specific details to give a thorough understanding of the measurement system; however, it will be apparent that the measurement system may be practiced without these specific details.

In order to avoid obscuring the measurement system, some well-known system configurations and descriptions are not disclosed in detail. Likewise, the drawings showing embodiments of the system are semi-diagrammatic and not to scale and, particularly, some of the dimensions are for the clarity of presentation and are shown greatly exaggerated in the drawing FIGs. The term coupled is intended herein to mean a direct or indirect physical contact between elements.

Figure 1:
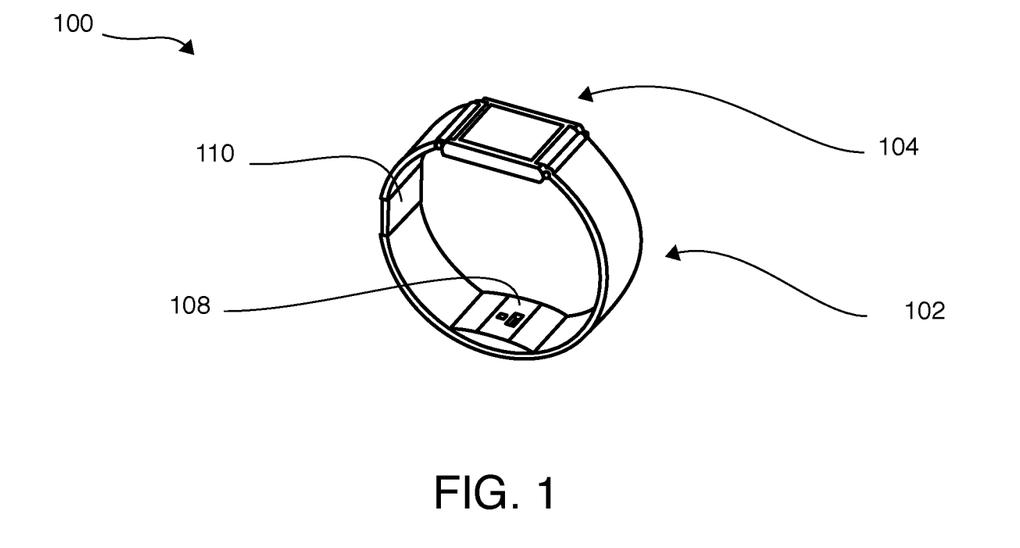
FIG. 1 is a top isometric view of the measurement system in a first embodiment.

Referring now to FIG. 1, therein is shown a top isometric view of the measurement system 100 in a first embodiment. The measurement system 100 can be implemented within a wearable device or clothing item such as a watch, a ring, a finger clamp, a finger glove, or other wearable item.

Illustratively, the measurement system 100 can include a pressure resistant structure such as a band 102 and a body 104 of a watch for example. The band 102 and the body 104 can provide a pressure resistant structure since the band 102 and the body 104 do not readily expand outward with increasing pressure, but instead constrain increasing pressure and exert the increasing pressure on a portion of the user in direct or indirect contact with the pressure resistant structure. For example, the pressure resistant structure could be a watch, a fitness band, a ring, an in-ear surface, an accessory for a mobile phone, or a combination thereof.

The band 102 can include a pressure inducer 108 and is contemplated to provide a non-elastic structure for constraining pressures exerted on a portion of a user in contact with the band 102, and compressing tissue between the pressure inducer 108 and the body 104. The pressure inducer 108 is described in greater detail with regard to FIGS. 3 and 4.

The pressure inducer 108 can provide a controlled pressure ramp contributing to, and enabling, highly accurate blood pressure readings utilizing a wearable electronic device. The pressure inducer 108 is further shown to be arranged on an opposite side of the band 102 from the body 104.

The pressure inducer 108 can therefore provide a pressure ramp in the direction of the body 104 where a light source, a photo detector, and a pressure sensor can be arranged. In alternative embodiments, the light source, the photo detector, the pressure sensor, or a combination thereof can be arranged on or formed integrally with the pressure resistant structure. Further, it is alternatively contemplated that the light source, the photo detector, the pressure sensor, or a combination thereof can be arranged or formed within the pressure inducer 108.

The band 102 can further include a mechanical adjustment mechanism 110 to ensure a universal fit. The mechanical adjustment mechanism 110 can be an adjustable clasp, an adjustable band, or even a screw for decreasing an interior area of the measurement system 100.

Figure 2:
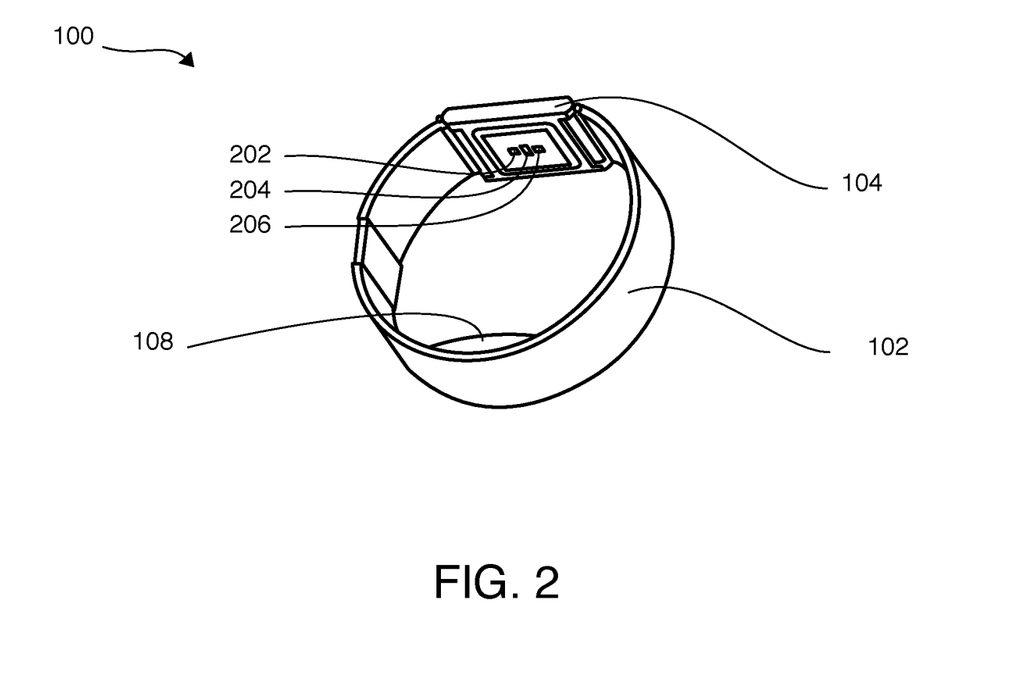
FIG. 2 is a bottom isometric view of the measurement system of FIG. 1.

Referring now to FIG. 2, therein is shown a bottom isometric view of the measurement system 100 of FIG. 1. The measurement system 100 is shown including the band 102 having the pressure inducer 108 opposite the body 104 including a light source 202, an optical sensor 204, and a pressure sensor 206.

The light source 202 and the optical sensor 204 can be combined to function as a pulse oximeter for detecting and reading volumetric fluid changes within a user along a controlled pressure ramp. As is shown, the light source 202 and the optical sensor 204 are both arranged within the body 104 facing the same direction.

The light source 202 and the optical sensor 204 therefore generate a reflective signal. That is, light emitted by the light source 202 is reflected and scattered by structures within the tissue of a user. This reflected light is then received by the optical sensor 204 as a volumetric data such as Photoplethysmography (PPG) data.

In alternative embodiments, the light source 202 and the optical sensor 204 can be on different areas of the band 102 to create a transmissive signal. With a transmissive signal, a portion of the light emitted by the light source 202 traverses through the tissue of the user and is received by the optical sensor 204.

The body 104 of the wearable can further contain a processor, such as an application specific integrated circuit for acquiring data from the optical sensor 204. The processor can further provide data acquisition from the pressure sensor 206. In alternative embodiments, the processor could be a remote processor.

Combined, the data from the pressure sensor 206 and the optical sensor 204 can provide volumetric fluid changes at different pressure levels. The different pressure levels can be provided by the controlled ramp of the pressure inducer 108 through a transition temperature range.

The pressure inducer 108, can be controlled by a micro controller, and can provide highly controlled pressure inputs for determining the volumetric fluid change measurement at various pressure levels. Illustratively, for example, the measurement system 100 could induce pressure on a user's wrist within the band 102 with the pressure inducer 108.

The measurement system 100 can detect both the pressure exerted on the user as well as a volumetric fluid change using the pressure sensor 206 and the optical sensor 204, respectively. The volumetric fluid change and the pressure can be correlated to provide a blood pressure reading of the user.

It is contemplated that the blood pressure reading can be stored in non-transitory computer readable media within the measurement system 100 and can be transmitted to another system for further processing and analysis. For example, it is contemplated that blood pressure readings could be shared or updated to a user's medical or training records at regular intervals.

Figure 3:
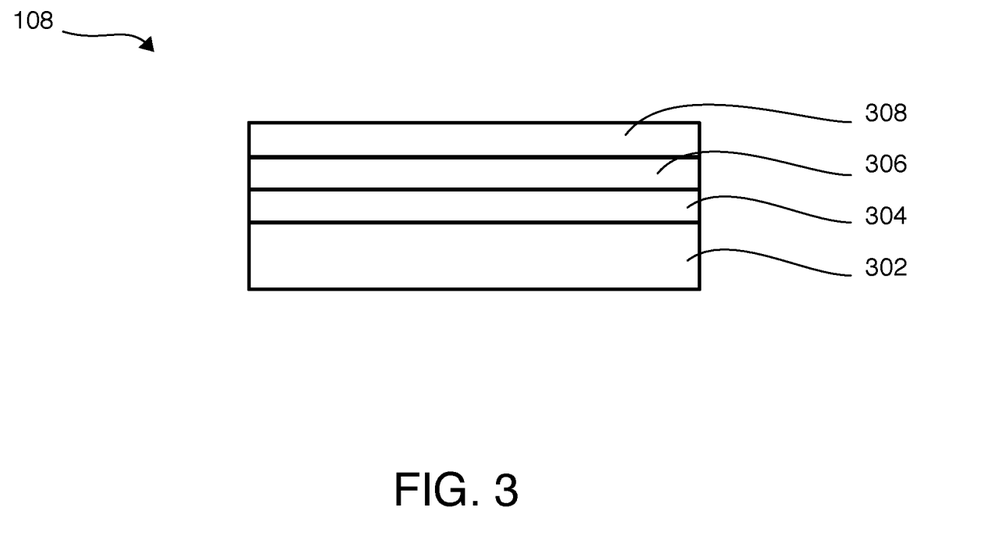
FIG. 3 is a side view of the pressure inducer of FIG. 1 in a released configuration.

Referring now to FIG. 3, therein is shown a side view of the pressure inducer 108 of FIG. 1 in a released configuration. The pressure inducer 108 can include a substrate 302 for providing a fixed support.

The substrate 302 can support an activation layer 304, a shape-memory layer 306, and a passivation layer 308. The activation layer 304 can include a flexible, thermally conductive material having a heating element powered by a current supply such as a battery contained within the body 104 of FIG. 1, for example.

The activation layer 304 can be controlled by a micro controller for precisely heating the shape-memory layer 306 in terms of both heating cycle times and heat intensities. The shape-memory layer 306 is contemplated to be made of a shape-memory material.

The shape-memory material can be a shape-memory polymer or shape-memory alloy. Shape-memory polymers can be engaged by increasing and decreasing temperature, for example by the activation layer 304. The activation layer 304 is layered on the shape-memory layer 306.

Some contemplated shape-memory polymers can also be engaged by activating an electric field or a magnetic field. In these alternative embodiments, it is further contemplated that the activation layer 304 could be replaced by an electromagnet or electric field inducing layers formed on the top and bottom of the shape-memory layer 306. In yet other contemplated embodiments, the light source 202 could be formed within flexible layers of the pressure inducer 108.

For descriptive clarity, the shape-memory layer 306 will be described with regard to a shape-memory alloy such as an alloy of copper-aluminum-nickel; nickel-titanium; or zinc, copper, gold and iron. More specifically, the shape-memory layer 306 is described with regard to Nitinol, an alloy of nickel and titanium.

In the present illustrative embodiment, the shape-memory layer 306 is contemplated to possess both shape-memory and super elastic properties. Shape-memory properties of the shape-memory layer 306 can be induced by shape-setting the shape-memory layer 306.

The shape-memory layer 306 can be shape-set by constraining the shape-memory layer 306 in a shape-set state, such as an arc, then heat treating the shape-memory layer 306 while in the shape-set state. It is contemplated that heat treating the shape-memory layer 306 can include bringing the shape-memory layer 306 to a high temperature, such as 400-550 degrees Celsius, and then rapidly cooling the shape-memory layer 306.

Illustratively, for example, the shape-memory layer 306 can maintain the arc shape, of the previous example, while the shape-memory layer 306 is in a shape-set state. The shape-set state can be an austenite state. In the austenite state, the shape-memory layer 306 can have a volume larger than the volume of the shape-memory layer 306 while in the deformable state. Coupling the shape-memory layer 306 between the pressure resistant structure and a user can allow the increase in volume of the shape-memory layer 306, to create or induce pressure onto tissue of the user. The activation layer 204 can be flexible and can follow the contour of the shape-memory layer in the shape-set state.

Cooling the shape-memory layer 306 below a transition temperature range can force the shape-memory layer 306 to enter a deformable state. The deformable state can be a martensite state. In the martensite state, the shape-memory layer 306 can have a volume smaller than the volume of the shape-memory layer 306 while in the shape-set state. Coupling the shape-memory layer 306 between the pressure resistant structure and a user, can allow the decrease in volume of the shape-memory layer 306 to cause less pressure on tissue of the user.

The pressure inducer 108 is depicted in the released configuration of FIG. 3 as having the shape-memory layer 306 in the deformable state. Alternatively, the pressure inducer 108 is depicted in the engaged configuration of FIG. 4 as having the shape-memory layer 306 in the shape-set state.

When the shape-memory layer 306 is in the deformable state, the shape-memory layer 306 can be deformed into the released configuration, which can be a flat or straight layer. The activation layer 304 can heat the shape-memory layer 306 and place the shape-memory layer 306 back into the shape-set state by increasing the temperature of the shape-memory layer 306 above the transition temperature range.

The shape-memory layer 306 can be placed back into the deformable state by lowering the temperature of the shape-memory layer 306 below the transition temperature range.

Illustratively, for example, the activation layer 304 could be turned off allowing the temperature of the shape-memory layer 306 to drop below the transition temperature by dropping back down to the body temperature of the user.

The shape-memory layer 306 differs from other materials in that when the shape-memory layer 306 is in the deformable state, atomic planes within the shape-memory layer 306 can be rearranged without causing slip, or permanent deformation. It has been found in some cases that the maximum amount of deformation in the deformable state that the shape-memory materials of the shape-memory layer 306 can hold without permanent damage is up to eight percent for some alloys. This compares with a maximum strain one-half a percent for conventional steels.

The transition temperature range of the shape-memory layer 306 can consist of four temperatures, those are a martensite start temperature, a martensite finish temperature, an austenite start temperature, and an austenite finish temperature. The martensite start temperature is the temperature when the shape-memory layer 306 begins to change from the austenite state to the martensite state while the martensite finish temperature is the temperature when the shape-memory layer 306 completes the transformation from the austenite state to the martensite state.

The austenite start temperature is the temperature when the shape-memory layer 306 begins to change from the martensite state to the austenite state while the austenite finish temperature is the temperature when the shape-memory layer 306 completes the transformation from the martensite state to the austenite state. It is contemplated that the austenite finish temperature of the shape-memory layer 306 should be above the body temperature of about thirty-seven degrees Celsius while the martensite finish temperature should be below or at body temperature.

Figure 4:
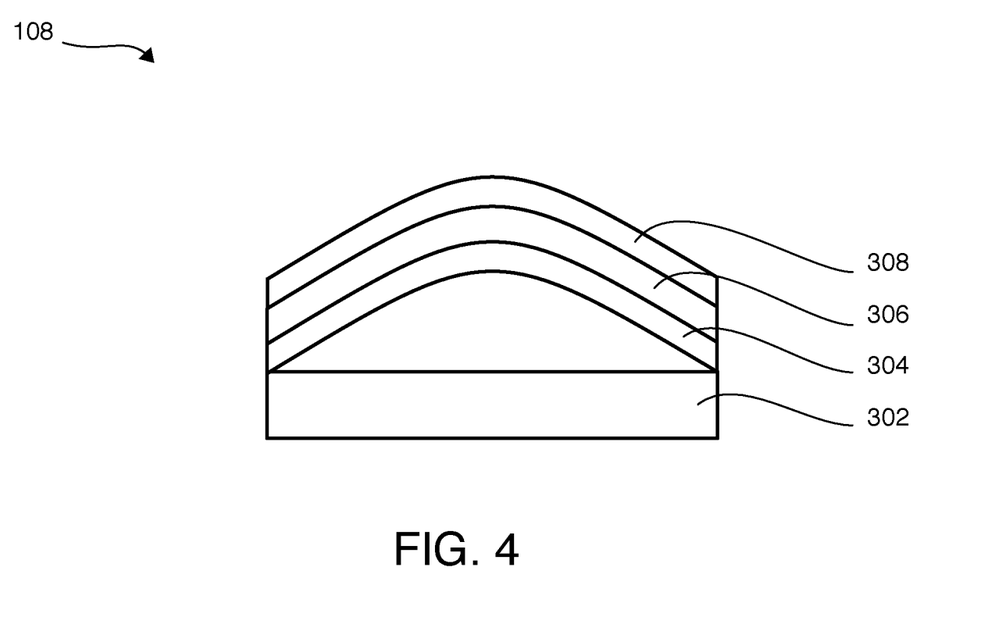
FIG. 4 is a side view of the pressure inducer of FIG. 1 in an engaged configuration.

Referring now to FIG. 4, therein is shown a side view of the pressure inducer 108 of FIG. 1 in an engaged configuration. The shape-memory layer 306 is shown in its shape-set state as an arced layer. The engaged configuration can increase pressure exerted on a portion of a user in contact with the pressure resistant structure.

The shape-memory layer 306 can be engaged by heating the shape-memory layer 306 above the transition temperature range with the activation layer 304. As the shape-memory layer 306 enters the shape-set state, the shape-memory layer 306 will transition from a flat layer depicted in FIG. 3 into the arced layer of FIG. 4.

The shape-memory layer 306 can provide enough force to bend the activation layer 304 below the shape-memory layer 306 and the passivation layer 308 above the shape-memory layer 306. The activation layer 304 conforms to a shape of the shape-memory layer 306 in the shape-set state. In alternate contemplated embodiments, the activation layer 304 could change its cross section rather than bend as a layer.

The shape-memory layer 306 can provide enough force to bend the activation layer 304 below the shape-memory layer 306 and the passivation layer 308 above the shape-memory layer 306. In alternate contemplated embodiments, the activation layer 304 could change its cross section rather than bend as a layer.

That is, the activation layer 304 could be thickest where the shape-memory layer 306 extends furthest from the substrate 302 and could be thinnest where the shape-memory layer 306 is closest to the substrate 302. In this alternate embodiment, the activation layer 304 would be in contact with both the shape-memory layer 306 and the substrate 302 when the shape-memory layer 306 is in the shape-set state.

The passivation layer 308 can be a thermally conductive layer for ensuring the shape-memory layer 306 can cool below the transition temperature range to enter the deformable state of FIG. 3. In the shape-set state of the shape-memory layer 306, the passivation layer 308 is forced away from the substrate 302, and when combined with the band 102 of FIG. 1, can create pressure within the wrist of a user.

This pressure can be detected by the pressure sensor 206 of FIG. 2 and can be correlated with pulse oximeter readings from the light source 202 and optical sensor 204, both of FIG. 2. The correlation of the pressure readings and pulse oximeter readings can provide blood pressure estimations.

More particularly, the volumetric data can be a PPG signal having a peak oscillatory amplitude. The volumetric data can be obtained at the same time the pressure data is obtained for a user. Illustratively, the pressure inducer can increase pressure on the user, which is detected by the pressure sensor 206 and which changes the volumetric data of the PPG signal detected by the optical sensor 204.

The peak oscillatory amplitude within the PPG signal is known to correspond to a mean blood pressure measured at the time of the peak oscillatory amplitude. A systolic blood pressure and a diastolic blood pressure can be calculated as a ratio above and below the mean blood pressure.

Further, the pressure detected by the pressure sensor 206 can be a controlled ramp by carefully controlling the temperature and heating of the shape-memory layer 306 through the transition temperature range. The temperature of the activation layer 304 can be precisely controlled by a micro controller throughout the transition temperature range.

Figure 5:
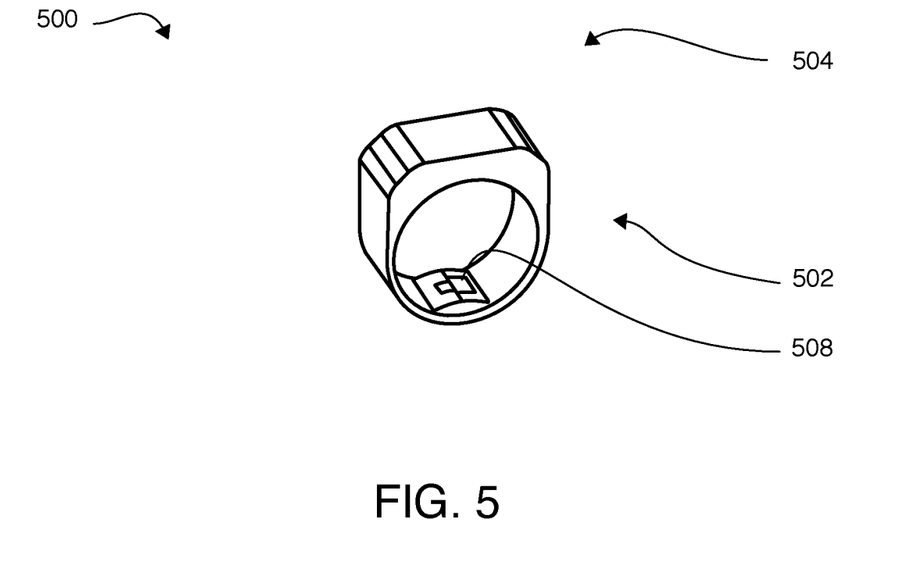
FIG. 5 is a top isometric view of the measurement system in a second embodiment.

Referring now to FIG. 5, therein is shown a top isometric view of the measurement system 500 in a second embodiment. The measurement system 500 can be implemented within a wearable device or clothing item such as a watch, a ring, a finger clamp, a finger glove, or other wearable item.

Illustratively, the measurement system 500 can include a pressure resistant structure such as a band 502 and a body 504 of a ring for example. The band 502 and the body 504 can provide a pressure resistant structure since the band 502 and the body 504 do not readily expand outward with increasing pressure, but instead constrain increasing pressure and exert the increasing pressure on a portion of the user in direct or indirect contact with the pressure resistant structure. For example, the pressure resistant structure could be a watch, a fitness band, a ring, an in-ear surface, an accessory for a mobile phone, or a combination thereof.

The band 502 can include a pressure inducer 508 and is contemplated to provide a non-elastic structure for constraining pressures exerted on a portion of a user in contact with the band 502, and compressing tissue between the pressure inducer 508 and the body 504. The pressure inducer 508 is described in greater detail with regard to FIGS. 3 and 4.

The pressure inducer 508 can provide a controlled pressure ramp contributing to, and enabling, highly accurate blood pressure readings utilizing a wearable electronic device. The pressure inducer 508 is further shown to be arranged on an opposite side of the band 502 from the body 504.

The pressure inducer 508 can therefore provide a pressure ramp in the direction of the body 504 where a light source, an optical sensor, and a pressure sensor can be arranged. The light source and the optical sensor can be combined to function as a pulse oximeter for detecting and reading volumetric fluid changes within a user along a controlled pressure ramp. The light source and the optical sensor can be arranged within the body 504 facing the same direction, toward the pressure inducer 508.

The light source and the optical sensor therefore generate a reflective signal. That is, light emitted by the light source is reflected and scattered by structures within the tissue of a user. This reflected light is then received by the optical sensor.

In alternative embodiments, the light source and the optical sensor can be on different areas of the band 502 to create a transmissive signal. With a transmissive signal, a portion of the light emitted by the light source traverses through the tissue of the user and is received by the optical sensor.

Figure 6:
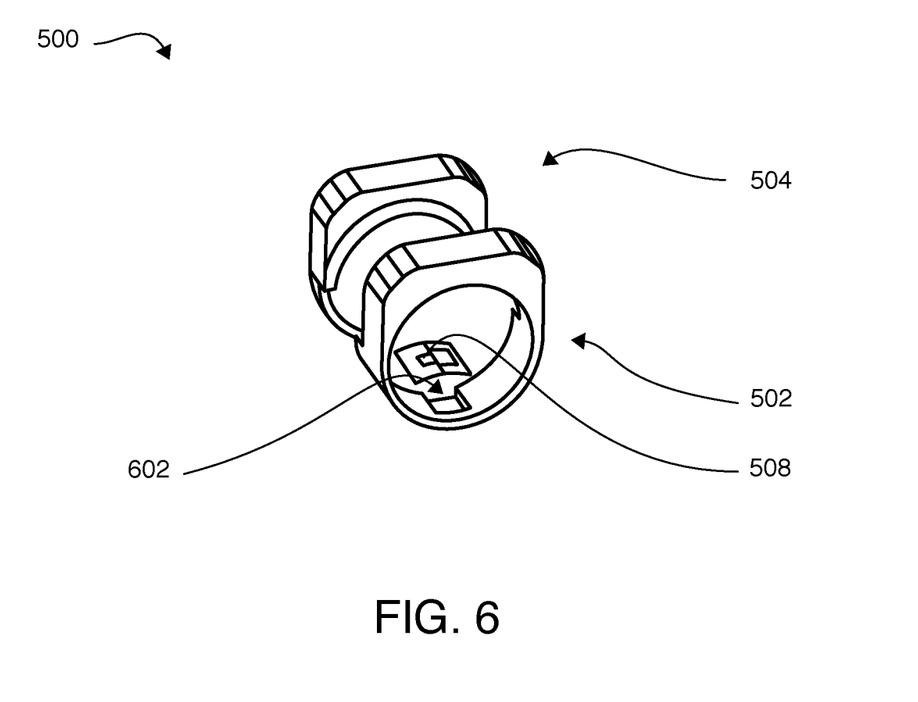
FIG. 6 is an exploded isometric view of the measurement system of FIG. 5.

Referring now to FIG. 6, therein is shown an exploded isometric view of the measurement system 500 of FIG. 5. The measurement system 500 is shown with the body 504 and the band 502 being split in half.

The band 502 is shown to have a pressure inducer cavity 602 opposite the body 504. The pressure inducer 508 can be inserted into the pressure inducer cavity 602 for rigidly mounting the pressure inducer 508 to the band 502.

Figure 7:
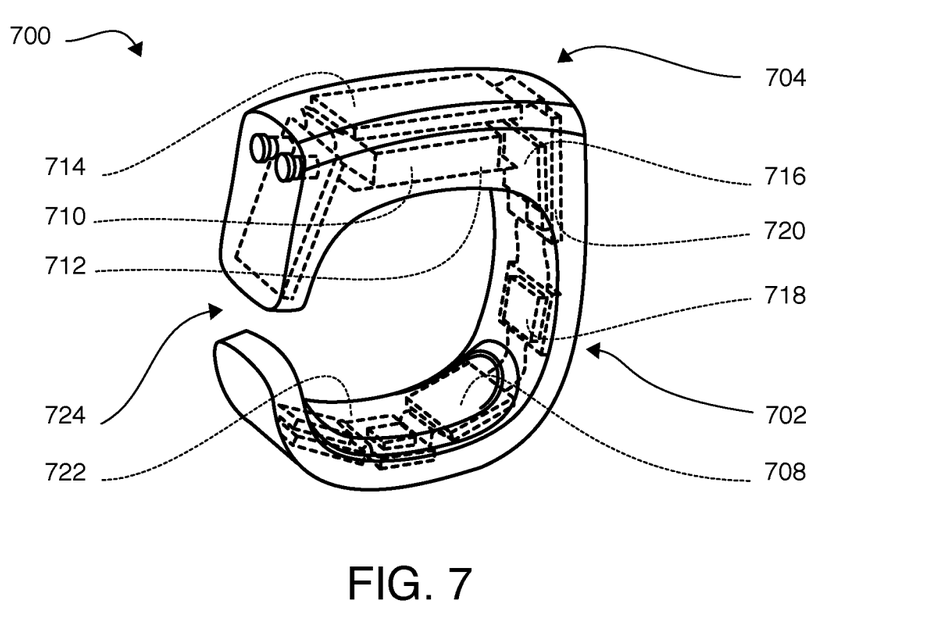
FIG. 7 is a top isometric view of the measurement system in a third embodiment.

Referring now to FIG. 7, therein is shown a top isometric view of the measurement system 700 in a third embodiment. The measurement system 700 can be implemented within a wearable device or clothing item such as a watch, a ring, a finger clamp, a finger glove, or other wearable item.

Illustratively, the measurement system 700 can include a pressure resistant structure such as a band 702 and a body 704 of a ring for example. The band 702 and the body 704 can provide a pressure resistant structure since the band 702 and the body 704 do not readily expand outward with increasing pressure, but instead constrain increasing pressure and exert the increasing pressure on a portion of the user in direct or indirect contact with the pressure resistant structure. For example, the pressure resistant structure could be a watch, a fitness band, a ring, an in-ear surface, an accessory for a mobile phone, or a combination thereof.

The band 102 can include a pressure inducer 708 and is contemplated to provide a non-elastic structure for constraining pressures exerted on a portion of a user in contact with the band 702, and compressing tissue between the pressure inducer 708 and the body 704. The pressure inducer 708 is described in greater detail with regard to FIGS. 3 and 4.

The pressure inducer 708 can provide a controlled pressure ramp contributing to, and enabling, highly accurate blood pressure readings utilizing a wearable electronic device. The pressure inducer 708 is further shown to be arranged on an opposite side of the band 702 from the body 704.

The pressure inducer 708 can therefore provide a pressure ramp in the direction of the body 704 where a light source 710, an optical sensor 712, and a pressure sensor 714 can be arranged.

The light source 710 and the optical sensor 712 can be combined to function as a pulse oximeter for detecting and reading volumetric fluid changes within a user along a controlled pressure ramp. As is shown, the light source 710 and the optical sensor 712 are both arranged within the body 704 facing the same direction, toward the pressure inducer 708.

The light source 710 and the optical sensor 712 therefore generate a reflective signal. That is, light emitted by the light source 710 is reflected and scattered by structures within the tissue of a user. This reflected light is then received by the optical sensor 712.

In alternative embodiments, the light source 710 and the optical sensor 712 can be on different areas of the band 702 to create a transmissive signal. With a transmissive signal, a portion of the light emitted by the light source 710 traverses through the tissue of the user and is received by the optical sensor 712.

The body 704 of the wearable can further contain a processor 716, such as an application specific integrated circuit for acquiring data from the optical sensor 712. The processor 716 can further provide data acquisition from the pressure sensor 714.

Combined, the data from the pressure sensor 714 and the optical sensor 712 can provide a volumetric fluid changes at different pressure levels. The different pressure levels can be provided by the controlled ramp of the pressure inducer 708 through the transition temperature range.

The pressure inducer 708, can be controlled by a micro controller 718, which can provide highly controlled current from a current source 720. The current source 720 can be a battery, capacitor, or other current source for heating the activation layer 304 of FIG. 3.

The micro controller 718 and the current source can together provide a controlled pressure ramp for determining the volumetric fluid change measurement at various pressure levels. Illustratively, for example, the measurement system 700 could induce pressure on a user's finger within the band 702 with the pressure inducer 708.

The pressure ramp, exerted by the pressure inducer, can exhibit known super elastic or shape memory force displacements over a variation of temperatures. That is, the physical shape of the shape-memory layer and amount of heat supplied to the shape-memory layer can both be used to carefully control the pressure ramp of the pressure inducer as specific temperatures are known to equate with the specific shape and state of shape-memory materials.

The measurement system 700 can detect both the pressure exerted on the user as well as a volumetric fluid change with the pressure sensor 714 and optical sensor 712, respectively. The volumetric fluid change and the pressure can be correlated to provide a blood pressure reading of the user.

Illustratively, for example, the volumetric data can be a PPG signal with a peak oscillatory amplitude corresponding in time to a mean blood pressure. That is, the pressure reading at time of the peak oscillatory amplitude of the volumetric data, will correlate to a mean blood pressure detected at the same time that the peak oscillatory amplitude is measured. A systolic blood pressure and a diastolic blood pressure can be calculated as a ratio above and below the mean blood pressure.

It has been unexpectedly discovered that this method of correlating the pressure reading to the peak oscillatory amplitude using the shape memory controlled pressure ramp allows a calibration-free, cuff-less blood pressure measurement to be obtained due to the controllable super elastic or shape memory force displacements over a known range of temperatures. Previous attempts required frequent re-calibrations due to greater variability in other previously used force inducing mechanisms.

The band 702 can further include a pressure plate 722 affixed to the passivation layer 308 of FIG. 3 of the pressure inducer 708. The pressure plate 722 can provide a larger surface area over which the pressure from the pressure inducer 708 can be distributed on the finger of a user.

The pressure plate 722 can also provide a heat sink allowing heat from the shape-memory layer 306 of FIG. 3 to diffuse out of the shape-memory layer 306 and into the pressure plate 722 allowing the shape-memory layer 306 to cool off faster and thereby enter the deformable state faster.

The band 702 can further be seen to include a gap 724. The gap can be relatively fixed within the rigid band 702 but could allow for minor movements or act to provide a pressure upper limit where the gap 724 increases once an upper pressure threshold is reached.

It is contemplated that the blood pressure reading can be stored in non-transitory computer readable media within the measurement system 700 and can be transmitted to another system for further processing and analysis. For example, it is contemplated that blood pressure readings could be shared or updated to a user's medical or training records at regular intervals.

Figure 8:
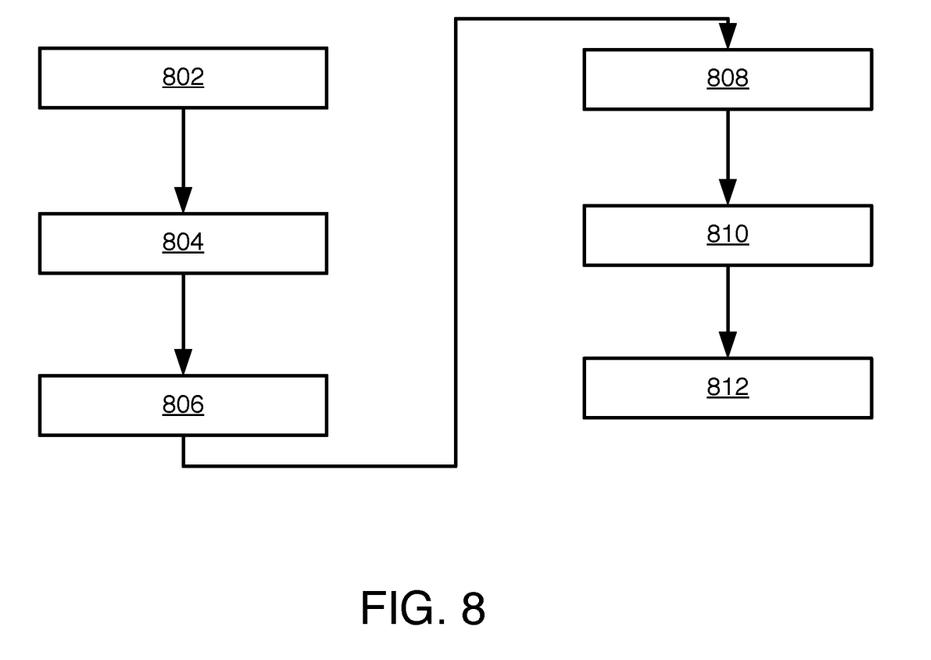
FIG. 8 is a method of manufacturing the measurement system.

Referring now to FIG. 8, therein is shown a method of manufacturing the measurement system. The method of manufacturing can include: providing a pressure resistant structure in a block 802; coupling a pressure inducer to the pressure resistant structure, the pressure inducer having an activation layer, and a shape-memory layer, the shape-memory layer configured to have a shape-set state and a deformable state, the activation layer configured to induce the shape-memory layer into the shape-set state and increase pressure exerted on a portion of a user in contact with the pressure resistant structure in a block 804; coupling a light source to the pressure resistant structure in a block 806; coupling an optical sensor to the pressure resistant structure and configured to detect signals from the light source in a block 808; coupling a pressure sensor to the pressure resistant structure, the pressure sensor configured to detect pressures exerted on the portion of the user in contact with the pressure inducer in a block 810; and coupling a processor to the optical sensor and the pressure sensor, the processor configured to correlate volumetric data from the optical sensor with pressure data from the pressure sensor and to provide a blood pressure measurement in a block 812.

Thus, it has been discovered that the measurement system furnishes important and heretofore unknown and unavailable solutions, capabilities, and functional aspects. The resulting configurations are straightforward, cost-effective, uncomplicated, highly versatile, accurate, sensitive, and effective, and can be implemented by adapting known components for ready, efficient, and economical manufacturing, application, and utilization.

While the measurement system has been described in conjunction with a specific best mode, it is to be understood that many alternatives, modifications, and variations will be apparent to those skilled in the art in light of the preceding description. Accordingly, it is intended to embrace all such alternatives, modifications, and variations, which fall within the scope of the included claims. All matters set forth herein or shown in the accompanying drawings are to be interpreted in an illustrative and non-limiting sense.

What is claimed is:

1. A measurement system comprising:
a pressure resistant structure;
a pressure inducer coupled to the pressure resistant structure, the pressure inducer having an activation layer layered on a shape-memory layer, the activation layer conforms to a shape of the shape-memory layer in a shape-set state, and the pressure inducer having an engaged configuration, the engaged configuration of the pressure inducer increasing pressure exerted on a portion of a user in contact with the pressure resistant structure;

a light source coupled to the pressure resistant structure;

an optical sensor coupled to the pressure resistant structure and configured to detect a signal from the light source;

a pressure sensor coupled to the pressure resistant structure, the pressure sensor configured to detect the pressure exerted on the portion of the user in contact with the pressure inducer; and a processor coupled to the optical sensor and the pressure sensor, the processor configured to correlate volumetric data from the optical sensor with pressure data from the pressure sensor and to provide a blood pressure measurement.

2. The system of claim 1 wherein the pressure inducer further includes a substrate and a passivation layer.

3. The system of claim 1 wherein the processor is an application specific integrated circuit for acquiring the volumetric data from the optical sensor and the pressure data from the pressure sensor.

4. The system of claim 1 further comprising a pressure plate coupled to the pressure inducer, the pressure plate configured to distribute the pressure exerted on the user from the pressure inducer.

5. The system of claim 1 further comprising a mechanical adjustment mechanism coupled to the pressure resistant structure, the mechanical adjustment mechanism for providing a universal fit.

6. A measurement system comprising:

a pressure resistant structure including a band and a body;

a pressure inducer coupled to the band, the pressure inducer having an activation layer and a shape-memory layer, the shape-memory layer configured to have a shape-set state and a deformable state, the activation layer layered on the shape-memory layer, the activation layer conforms to a shape of the shape-memory layer in the shape-set state, and the activation layer configured to induce the shape-memory layer into the shape-set state and increase pressure exerted on a portion of a user in contact with the pressure resistant structure;

a light source coupled to the body;

an optical sensor coupled to the body and configured to detect a signal from the light source;

a pressure sensor coupled to the pressure resistant structure, the pressure sensor configured to detect the pressure exerted on the portion of the user in contact with the pressure inducer; and a processor coupled to the optical sensor and the pressure sensor, the processor configured to correlate volumetric data from the optical sensor with pressure data from the pressure sensor and to provide a blood pressure measurement.

7. The system of claim 6 wherein the shape-memory layer is a shape-memory polymer or a shape-memory alloy.

8. The system of claim 6 wherein the activation layer is configured to induce the shape-memory layer into the shape-set state by increasing heat.

9. The system of claim 6 further comprising a micro controller coupled to the pressure inducer, the micro controller configured to control a current source for heating the activation layer and providing a controlled pressure ramp.

10. A method of manufacturing a measurement system comprising:

providing a pressure resistant structure;

coupling a pressure inducer to the pressure resistant structure, the pressure inducer having an activation layer layered on a shape-memory layer, the activation layer conforms to a shape of the shape-memory layer in a shape-set state, and the pressure inducer having an engaged configuration, the engaged configuration of the pressure inducer increasing pressure exerted on a portion of a user in contact with the pressure resistant structure;

coupling a light source to the pressure resistant structure;

coupling an optical sensor to the pressure resistant structure and configured to detect a signal from the light source;

coupling a pressure sensor to the pressure resistant structure, the pressure sensor configured to detect the pressure exerted on the portion of the user in contact with the pressure inducer; and coupling a processor to the optical sensor and the pressure sensor, the processor configured to correlate volumetric data from the optical sensor with pressure data from the pressure sensor and to provide a blood pressure measurement.

11. The method of claim 10 wherein coupling the pressure inducer further includes coupling the pressure inducer having a substrate and a passivation layer.

12. The method of claim 10 wherein coupling the processor includes coupling an application specific integrated circuit for acquiring the volumetric data from the optical sensor and the pressure data from the pressure sensor.

13. The method of claim 10 further comprising coupling a pressure plate to the pressure inducer, the pressure plate configured to thermally conduct heat away from the pressure inducer.

14. The method of claim 10 further comprising coupling a mechanical adjustment mechanism to the pressure resistant structure, the mechanical adjustment mechanism for providing a universal fit.

15. The method of claim 10 wherein:

providing the pressure resistant structure includes providing a band and a body;

coupling the pressure inducer includes coupling the pressure inducer to the band, the pressure inducer having the activation layer and the shape-memory layer, the shape-memory layer configured to have the shape-set state and a deformable state, the activation layer configured to induce the shape-memory layer into the shape-set state to provide the engaged configuration and increase the pressure exerted on the portion of the user in contact with the pressure resistant structure;

coupling the light source includes coupling the light source to the body; and coupling the optical sensor includes coupling the optical sensor to the body.

16. The method of claim 15 wherein coupling the pressure inducer includes coupling the pressure inducer having the shape-memory layer formed from a shape-memory polymer or a shape-memory alloy.

17. The method of claim 15 wherein coupling the pressure inducer includes coupling the pressure inducer with the activation layer configured to distribute the pressure exerted on the user from the pressure inducer.

18. The method of claim 15 further comprising coupling a micro controller to the pressure inducer, the micro controller configured to control a current source for heating the activation layer and providing a controlled pressure ramp.

* * * * *